(12) United States Patent
Epner et al.

(10) Patent No.: US 10,660,864 B2
(45) Date of Patent: *May 26, 2020

(54) USE OF AMERICAN GINSENG TO COUNTERACT CANNABIS-INDUCED INTOXICATION

(71) Applicant: ENGEN MEDICAL CORPORATION, San Diego, CA (US)

(72) Inventors: Paul Epner, San Diego, CA (US); Richard Zimmer, III, Mandeville, LA (US); Bill W. Massey, Heber Springs, AR (US)

(73) Assignee: ENGEN MEDICAL CORPORATION, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/426,860

(22) Filed: May 30, 2019

(65) Prior Publication Data

US 2019/0274971 A1    Sep. 12, 2019

Related U.S. Application Data

(63) Continuation-in-part of application No. 15/863,266, filed on Jan. 5, 2018, now Pat. No. 10,350,253.

(51) Int. Cl.
*A61K 36/00* (2006.01)
*A61K 31/045* (2006.01)
*A61K 9/00* (2006.01)

(52) U.S. Cl.
CPC ............ *A61K 31/045* (2013.01); *A61K 9/006* (2013.01)

(58) Field of Classification Search
CPC ...................................................... A61K 36/00
USPC ........................................................ 424/725
See application file for complete search history.

(56) References Cited

U.S. PATENT DOCUMENTS 9,572,364 B2 * 2/2017 Langan .................. A23L 27/86

* cited by examiner

*Primary Examiner* — Michael V Meller
(74) *Attorney, Agent, or Firm* — Juan J. Lizarraga

(57) ABSTRACT

A composition and method for the use of *Panax quinquefolius* for the attenuation of *Cannabis*-induced dysphoria where dosage can be effectively administered in a gum base cold pressed into a tablet containing at least 300 mg of *Panax quinquefolius* and Maltitol, Sorbitol, Isomalt, Xylitol, natural & artificial flavors, vegetarian magnesium stearate, Sucralose and Silicon dioxide. A composition and method for the use of falcarinol for the attenuation of *Cannabis*-induced dysphoria and reverse *cannabis* tolerance where the dosage of at least 30 mg can be effectively administered for buccal absorption.

2 Claims, No Drawings

USE OF AMERICAN GINSENG TO COUNTERACT CANNABIS-INDUCED INTOXICATION

This application is a Continuation-in-part of application Ser. No. 15/863,266 (the '266 application') filed Jan. 5, 2018, co-owned with the present invention. The '266 application is incorporated here by reference for all purposes, and with respect to all of which the present invention claims priority under United States Patent Law.

BACKGROUND OF THE INVENTION

*Cannabis* (aka marijuana) is a genus of flowering plants that consists of three subspecies, *Cannabis sativa, Cannabis indica*, and *Cannabis ruderalis. Cannabis* produces hundreds of cannabinoids, which are terpeno-phenolic compounds. Some of these cannabinoids produce psychoactive effects (e.g. delta-9-tertrahydrocannabinol) whereas other cannabinoids are biologically-active and produce wide-ranging effects as disparate as conjunctive vasodilation, immune system regulation, stimulation of appetite, sleep-induction, and analgesia. Medical use of *Cannabis* is practiced today and has a history going back thousands of years, however, the medical utility of *Cannabis* is a topic of much contention. Several states have legalized the recreational and medical use of *Cannabis* and more states have placed *Cannabis* legalization on ballots for the voters of these states to determine its legal status. Currently, the US Federal government does not recognize the medical utility of *Cannabis* but has not interceded in the sale and distribution of *Cannabis* in those states where its use has been legalized. The eventual legal status of *Cannabis* at the federal level is uncertain. Despite the confusing and evolving legal status of *Cannabis*, it is one of the most commonly-used psychoactive substances in the world, exceeded only by ethanol-containing beverages, tobacco (nicotine), and coffee (caffeine).

One of the known biological effects of the consumption of *cannabis* is intoxication via psychoactive cannabinoids (e.g. delta-9-tetrahydrocannabinol). The psychoactive effects of *cannabis* are the reason it is used as a recreational intoxicant. The mechanism for *Cannabis*-induced intoxication is via agonism of cannabinoid subtype 1 (CB1) receptors. While the intoxication from *cannabis* is usually described as pleasurable, high doses of *cannabis* can result in dysphoria, including panic, generalized anxiety, and adverse bodily sensations. The lack of quality control and great differences in cannabinoid content between *cannabis* strains can result in some *cannabis* extracts to be extremely potent, and more likely to induce high-dose *cannabis*-induced dysphoria. This risk is increased when the *cannabis* is ingested as an edible form (e.g. *cannabis*-infused brownies, cookies, and lozenges). It is proposed that these dysphoric effects of high-dose *cannabis* would be reversed by chemical antagonists or inverse agonists of the CB1 receptor.

SUMMARY OF THE INVENTION

It is an object of this invention to provide a composition of *Panax quinquefolius* comprising a dosage in an amount effective for the attenuation of *Cannabis*-induced dysphoria in a human.

It is a further object of this invention to provide the composition of *Panax quinquefolius* within a gum base for efficacious delivery to the user through the ordinary process of gum chewing, where the gum base further comprises Maltitol, Sorbitol, Isomalt, Xylitol and other components.

It is a further object of this invention to provide a composition to reverse the intoxication in a human intoxicated by *cannabis* use comprising administering to said human a therapeutically effective amount of a composition of falcarinol where the amount of falcarinol is at least 30 mg and where the composition is a formulation that provides for buccal absorption.

It is a further object of this invention to provide a composition to reverse *cannabis* tolerance in a human *cannabis* user comprising administering to said human a therapeutically effective amount of a composition of falcarinol where the amount of falcarinol is at least 30 mg and where the composition is a formulation that provides for buccal absorption.

It is a further object of this invention to provide a method for detoxification of a human comprising administering a therapeutically effective amount of a composition containing American Ginseng that reduces the psychotropic activity caused by the consumption of *cannabis* by said human.

It is a further object of this invention to provide a method for detoxification of a human comprising administering a therapeutically effective amount of a composition containing falcarinol that reduces the psychotropic activity caused by the consumption of *cannabis* by said human.

It is a further object of this invention to provide a composition and method for reversal of *cannabis* tolerance in a human by administering a therapeutically effective amount of a composition containing falcarinol.

DETAILED DESCRIPTION OF THE INVENTION

The present invention described herein is the use of *Panax quinquefolius* (aka American Ginseng), including any processed (e.g. extracts, conjugates, heated, cooked, etc.) or unprocessed form of the plant, including roots, leaves and seeds, for the attenuation of *Cannabis*-induced dysphoria incorporated within a gum base with the below included ingredients for efficacious delivery to the user through the ordinary process of gum chewing. The gum base is formulated utilizing a cold pressed manufacturing process to incorporate all of the ingredients with heightened efficacy into a circular half inch diameter tablet. The ingredients incorporated into the gumbase are, Maltitol, Sorbitol, Isomalt, Xylitol, American Ginseng (African *Panax quinquefolius*) 300 mg per piece, natural & artificial flavors, vegetarian magnesium stearate, Sucralose and Silicon dioxide.

*Panax quinquefolius* is a herbaceous perennial plant in the ivy family, commonly used as herbal medicine. American ginseng was formerly particularly widespread in the forested regions of the Eastern United States, Appalachian and Ozark regions. However, due to its popularity and destruction of its habitat, the wild plant has been overharvested, and is rare in most parts of the United States and Canada. Currently, most American ginseng is grown commercially and is not wild-harvested. American ginseng is used for a wide variety of ailments in herbal medicine, from improving digestion, to improving immune function, to treating insomnia and anxiety. Approximately 200 substances have been isolated from ginseng including ginsenosides, polyacetylenes, alkaloids, polysaccharides, oligosaccharides, oligopeptides, phenolic compounds, lipids, vitamins, and minerals (Kolodziej et al., Chemical composition and chosen bioactive properties of *Panax quinquefolius* extracts. Chemija 24(2):151-159, 2013). Nonvolatile ginsenosides and falcarinol, a natural pesticide and fatty alcohol, are believed to be the main pharmacologically-active ginseng constituents (Kolodziej et al., Chemical composition and chosen bioactive properties of *Panax quinquefolius* extracts. Chemija 24(2):151-159, 2013).

Of special interest to *cannabis*-induced dysphoria, is the presence of falcarinol in American ginseng. Falcarinol is found at concentrations of up to 14% in the roots of *Panax quinquefolius* (Kolodziej et al., Chemical composition and chosen bioactive properties of *Panax quinquefolius* extracts. Chemija 24(2):151-159, 2013). Falcarinol is found in other root vegetables such as carrots, beets and parsnips. Falcarinol is a fungicide produced by root vegetables. Roots are particularly susceptible to fungi due to them being in contact with soil containing fungi and soil being an ideal growth medium for fungi (e.g. dark, moist, undisturbed). The falcarinol prevents the growth of fungi on the root surface and preserves the root. Falcarinol contains special properties with regard to reducing the psychoactive effects of *cannabis*. Most importantly, falcarinol has been shown to be a potent inverse agonist at the CB1 receptor, and thus would reverse the effects of CB1 agonism, and thereby attenuate *cannabis*-induced dysphoria (Leonti et al., Falcarinol is a covalent cannabinoid CB1 receptor antagonist and induces pro-allergic effects in skin. Biochemical Pharmacology 79(12):1815-1826, 2010). American ginseng, via Falcarinol's CB1 inverse agonist properties, would thereby attenuate *cannabis*-induced dysphoria.

The present invention as further described herein comprises the use of any root vegetable containing falcarinol including any processed (e.g. extracts, conjugates, heated, cooked, etc.) or unprocessed form of the plant, including roots, leaves and seeds, for the attenuation of *Cannabis*-induced dysphoria, in any formulation of at least 30 mg of falcarinol that provides for buccal absorption comprising dissolvable films, sprays, lozenges, tincture, dissolvable pills and tablets. Buccal absorption is an ideal route of administration for reversal of *cannabis*-induced intoxication by virtue of being rapid, going straight into the blood through the buccal mucosa without having to go through the digestive tract and liver. Rapid onset of action is of clinical importance in cases of intoxication, as one would want to reduce the adverse effects of *cannabis* very quickly.

The present invention as further described herein comprises the use of any root vegetable containing falcarinol including any processed (e.g. extracts, conjugates, heated, cooked, etc.) or unprocessed form of the plant, including roots, leaves and seeds, for the reversal of *Cannabis*-tolerance, in any formulation of at least 30 mg falcarinol that provides for buccal absorption comprising dissolvable films, sprays, lozenges, tincture, dissolvable pills and tablets. Tolerance is developed in response to persistent, repeated drug exposure, and is an attempt to re-establish physiological homeostasis. In the case of an agonist like the psychoactive cannabinoid THC, THC produces psychoactive effects by activating the CB1 receptor. The organism adapts by reducing the number of CB1 receptors on the brain cell surface, thereby decreasing the magnitude of THC effects by reducing THC-induced signaling through CB1 receptor agonism. This adaptive response helps to bring these signaling activities into homeostasis. An inverse agonist at the CB1 receptor, like falcarinol, would have the opposite effect as THC, increasing the number of CB1 receptors on the brain cell surface, increasing the sensitivity and strength of the THC-induced signaling, and reversing tolerance to THC.

It is an object of this invention to provide a method for detoxification comprising administering a therapeutically effective amount of a composition containing American Ginseng that reduces the psychotropic activity caused by the consumption of *cannabis*.

It is a further object of this invention to provide a method for detoxification of a human intoxicated by *cannabis* use comprising administering a therapeutically effective amount of a composition containing falcarinol that reduces the psychotropic activity caused by the consumption of *cannabis* where the amount of falcarinol is at least 30 mg and where the composition is a formulation that provides for buccal absorption.

It is a further object of this invention to provide a method for reversal of *cannabis* tolerance in a human comprising administering a therapeutically effective amount of a composition containing falcarinol to increase the number of CB1 receptors on the brain cell surface, increasing the sensitivity and strength of the THC-induced signaling, and reversing tolerance to THC where the amount of falcarinol is at least 30 mg and where the composition is a formulation that provides for buccal absorption.

What is claimed is:

1. A method of reversing *cannabis* tolerance in a human *cannabis* user consisting essentially of administering to the human *cannabis* user in need thereof via buccal absorption a therapeutically effective amount of a *Panax quinquefolius* extract consisting essentially of falcarinol wherein the buccal absorption is via a dissolvable film, spray, lozenge, tincture, dissolvable pill or tablet to effectively reverse the *cannabis* tolerance in the human *cannabis* user.

2. A method of reversing the intoxication in a human intoxicated by *cannabis* use consisting essentially of administering to the human in need thereof via buccal absorption a therapeutically effective amount of a *Panax quinquefolius* extract consisting essentially of falcarinol wherein the buccal absorption is via a dissolvable film, spray, lozenge, tincture, dissolvable pill or tablet to effectively reverse the intoxication in the human intoxicated by *cannabis* use.

* * * * *